United States Patent [19]
Craps

[11] 3,933,999
[45] Jan. 20, 1976

[54] ORGANIC COMPOUNDS

[75] Inventor: Lucien Craps, Basel, Switzerland

[73] Assignee: Sandoz Ltd., (Sandoz AG), Basel, Switzerland

[22] Filed: Dec. 17, 1973

[21] Appl. No.: 425,121

[30] Foreign Application Priority Data
Dec. 22, 1972 Switzerland.................... 018770/72

[52] U.S. Cl. .................. 424/31; 424/274; 424/273; 424/33
[51] Int. Cl.² ...................... A61K 9/32; A61K 9/58; A61K 31/40; A61K 31/415
[58] Field of Search ................ 424/31, 274, 273, 33

[56] References Cited
UNITED STATES PATENTS
3,097,212   7/1963   Jucker et al. .................. 260/293.83

OTHER PUBLICATIONS

Handbook of Non-Prescription Drugs – Published by the American Pharm. Assoc., Wash. D.C., (Sept. 1967), pp. 19, 20 & 24 & 25.

*Primary Examiner*—Donald B. Moyer
*Attorney, Agent, or Firm*—Gerald D. Sharkin; Robert S. Honor

[57] ABSTRACT

The invention concerns novel combinations of active agents a) 1-methyl-2-[2-(α-methyl-p-chlorodiphenylmethyloxy)ethyl]pyrrolidine and b) a non-toxic sympathicomimetic agent having a peripheral vasoconstrictive effect, useful in the treatment of rhinitis.

15 Claims, No Drawings

ORGANIC COMPOUNDS

The present invention relates to the antihistaminic agent, 1-methyl-2-[2-(α-methyl-p-chlorodiphenylmethyloxy)ethyl]pyrrolidine of formula I,

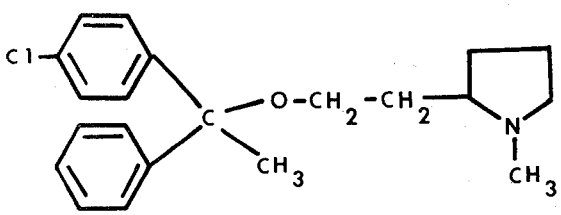

I known under the international name Mecloprodin (or Clemastin).

The present invention provides a pharmaceutical composition incorporating as active agents a. 1-methyl-2-[2-(α-methyl-p-chlorodiphenylmethyloxy)ethyl]pyrrolidine in free base form or in pharmaceutically acceptable acid addition salt form, and b. a non-toxic sympathicomimetic agent having a peripheral vasoconstrictive effect, in free base form or in pharmaceutically acceptable acid addition salt form.

Examples of sympathicomimetic agents are preferably enterally effective sympathicomimetic agents, such as sympathicomimetic 2-amino-1-phenylalkan-1-ol derivatives, e.g. 2-amino-1-phenylpropanol, 2-methylamino-1-phenylpropanol, 1-(3′-hydroxyphenyl)-2-methylaminoethanol or 1-phenyl-2-diethylaminopropanol, or agents suitable for local use, e.g., imidazoline derivatives such as naphazoline, xylometazoline or tetryzoline. 2-amino-1-phenylpropanol, for which the name phenylpropanolamine is hereinafter used, is especially suitable in this respect. This has been described inter alia in the British Pharmaceutical Codex 1968. The sympathicomimetic agent preferably has strong peripheral vasoconstrictive properties. Further desirable properties are a rapid onset of the peripheral vasoconstrictive effect and a long duration of the effect, as well as good tolerance.

The active agents a) and b) are in general known and may be prepared by conventional chemical methods and purified in conventional manner to produce a pharmaceutically acceptable, i.e., non-toxic, form.

The combination of active agent a) and active agent b) is useful in the treatment of rhinitis, for example acute, allergic, banal, viral, and vasomotor rhinitis and rhinitis due to bronchitis, sinusitis and rickets, wherein the combination supplements the exudation-inhibiting effect of Mecloprodin by a vasoconstriction of the peripheral vessels in the nasal area and additionally exhibits a synergistic effect over active agent a) and active agent b), with a rapid onset and long-lasting activity and with few side effects, e.g., little fatigue, as indicated by standard tests; for example, on peroral administration of a combination of 1 mg of active agent a) and from 10 to 60 mg of active agent b) twice a day to patients, a decrease of nasal congestion was observed by measuring the nasal flow resistance in healthy patients before and after nasal mucous membrane swelling provoked by histamine spray and also in patients suffering from vasomotor, allergic and acute rhinitis.

For the above-mentioned use the dose of active agents a) and b) and their ratio by weight will of course vary depending on the compound employed, mode of administration and condition to be treated. However, in general satisfactory results are obtained when active agent a) is administered at a daily dosage of from about 0.02 mg to about 0.15 mg per kg animal body weight and at a weight ratio of active agent a) to active agent b) of from 1:10 to 1:60, preferably 1:25 to 1:50, especially 1:30 to 1:50. The combination is conveniently given in sustained release form or in divided doses two to four times a day. For the larger mammals the total daily dosage is in the range from about 2 to about 6 mg of active agent a), preferably from 2 to 4 mg. Dosage forms comprise from about 1 to 3 mg of active agent a) when to be administered twice daily.

A preferred unit dosage form has 1 mg of active agent a) and from 30 to 50 mg of active agent b).

Each of the active agents may be in free base form or in pharmaceutically acceptable acid addition salt form. Such salt forms are known and exhibit the same order of activity as the free base forms. The free base forms may be converted into the pharmaceutically acceptable acid addition salt forms in conventional manner and vice versa. Representative acids for salt formation include the mineral acids such as hydrochloric acid, hydrobromic acid and sulphuric acid and the organic acids such as aliphatic acids, such as acetic acid, polycarboxylic acids such as fumaric acid and tartaric acid and organic sulphonic acids such as methane sulphonic acid or benzene sulphonic acid. The preferred acid for agent a) is fumaric acid. The preferred acid for agent b) when phenylpropanolamine is hydrochloric acid.

Each of the active agents may be associated with pharmaceutical carriers and diluents in conventional manner. Example of pharmaceutical carriers and diluents are inert organic or inorganic diluents such as organic or inorganic calcium salts, sodium salts, mannitol, lactose, talc or colloidal silicic acid; disintegrating agents such as starch or alginic acid; binding agents such as polyvinylpyrrolidone, gelatin or cellulose derivatives; lubricating agents such as stearic acid and its salts, e.g., the magnesium salt; suspending agents such as methylcellulose, tragacanth and sodium alginate; wetting agents such as lecithin, and flavouring, colouring and preserving agents.

Pharmaceutical compositions comprising one or both active agents in association with a pharmaceutical carrier or diluent may be in liquid or solid form, for example, for local or enteral administration, preferably enteral administration. The preferred mode of administration is oral administration. Pharmaceutical compositions may be prepared by conventional techniques.

The present invention also provides a process for the production of a pharmaceutical composition including the step of bringing together active agent a) and active agent b). A pack may be provided which contains separately active agents a) and b) until required for administration as a composition as mentioned above.

Examples of compositions for enteral administration are inter alia tablets, capsules, dragees, syrups, drops and suppositories. Examples of suitable compositions for local administration are sprays, drops and ointments.

The preferred composition from the standpoint of ease of administration is a capsule or tablet.

At least one of the active agents may be associated with a retard agent. Preferred compositions have the active agent b) associated with a retard agent to delay absorption of active agent b) on administration with respect to active agent a).

Suitable retard agents are, for example, polyvinylacetate, vinyl copolymers, acrylate copolymers, methacrylate copolymers, higher fatty alcohols and other wax-like substances. The active agents may be additionally coated with a porous insoluble film. Alternatively the active agent may be in the form of a difficultly soluble salt or complex, e.g. a resinate, especially in the case of phenylpropanolamine.

Active agent b) may be incorporated in a core within an outer layer incorporating active agent a) so that the liberation of active agent b) is slightly retarded with respect to active agent a). For instance a coated tablet may be formulated having a kernel containing active agent b) within a coating containing active agent a).

The following non-limitative Examples illustrate the invention, 1. indicates equivalent to 1 mg free base form Phenylpropanolamine is present in hydrochloride form.

EXAMPLE 1: Capsules
Composition:

| | | |
|---|---|---|
| Mecloprodin hydrogen fumarate | 1.34[1]) | mg/dose |
| Phenylpropanolamine | 30.00 | ″ |
| Mannitol | 208.66 | ″ |
| Microcrystalline cellulose | 75.00 | ″ |
| Talc | 15.00 | ″ |
| yields one capsule of | 330.00 | mg |

EXAMPLE 2: Tablets
Composition:

| | | |
|---|---|---|
| Mecloprodin hydrogen fumarate | 1.34[1]) | mg/dose |
| Phenylpropanolamine | 30.00 | ″ |
| Lactose | 243.66 | ″ |
| Maize starch | 33.00 | ″ |
| Polyvinyl pyrrolidone (Kollidon 30) | 20.00 | ″ |
| Magnesium stearate | 2.00 | ″ |
| yields one tablet of | 330.00 | mg |

The active agents are mixed with the lactose and the maize starch, the mixture is moistened with polyvinyl pyrrolidone dissolved in a 3-fold quantity of 50 % ethanol and is granulated. The granulate which has been ground with magnesium stearate is tabletted as usual.

EXAMPLE 3: Tablets
Composition:

| | | |
|---|---|---|
| Mecloprodin hydrogen fumarate | 1.34[1]) | mg/dose |
| Phenylpropanolamine | 50.00 | ″ |
| Magnesium stearate | 58.66 | ″ |
| Calcium-hydrogen phosphate-2-hydrate | 45.00 | ″ |
| Cellulose acetate phthalate | 30.00 | ″ |
| Polyvinyl acetate | 75.00 | ″ |
| yields one tablet of | 260.00 | mg |

The active agents are mixed, moistened with one tenth by weight of ethanol and granulated and tabletted in the usual manner.

EXAMPLE 4: Coated tablets
Composition of the kernel:

| | | |
|---|---|---|
| Phenylpropanolamine | 50.00 | mg/dose |
| Magnesium stearate | 20.00 | ″ |
| Calcium-hydrogen phosphate-2-hydrate | 15.00 | ″ |
| Cellulose acetate phthalate | 10.00 | ″ |
| Polyvinyl acetate | 25.00 | ″ |
| yields one kernel of | 120.00 | ″ |

Composition of the coating:

| | | |
|---|---|---|
| Mecloprodin hydrogen fumarate | 1.407 | mg/dose |
| Lactose | 272.993 | ″ |
| Maize starch | 33.000 | ″ |
| Polyvinyl pyrrolidone (Kollidon 30) | 20.000 | ″ |
| Colouring agent | 0.600 | ″ |
| Magnesium stearate | 2.000 | ″ |
| Total | 330.000 | ″ |

The production of the kernels is effected as described in Example 3:

A granulate is produced from the ingredients contained in the coating in a manner analogous to that described in Example 2, and this granulate is worked up together with the kernels into coated tablets of 450 mg each.

EXAMPLE 5

In analogous manner to any one of Examples 1 to 4 there are produced compositions having the following ratios of active Mecloprodin to phenylpropanolamine 1:10; 1:15; 1:20; 1:25; 1:35; 1:40; 1:45; 1:55 based on 50 mg of active phenylpropanolamine/dose.

EXAMPLE 6

In analogous manner to any one of Examples 1 to 4 there are produced compositions wherein the amount of active phenylpropanolamine is 30 mg/dose with appropriate amounts of Mecloprodin.

EXAMPLE 7

Suppositories (2.0 g) and dragees (400 mg) are manufactured using conventional techniques using the amounts of Mecloprodin and phenylpropanolamine of any of Examples 1 to 6 with conventional suppository and dragee diluents and carriers and are effective agents for the relief of rhinitis when administered at the equivalent dose of 2 to 6 mg of Mecloprodin a day.

EXAMPLE 8

Syrups, drops and ointments are manufactured using conventional techniques using the amounts of Mecloprodin and phenylpropanolamine of any of Examples 1 to 6 per 5 mg (syrups), 5 ml (drops) and 1 g (ointments) using the appropriate conventional diluents and carriers and are effective agents for the relief of rhinitis when administered at a dose of 2 to 6 mg of Mecloprodin a day.

EXAMPLE 9

In analogous manner to Examples 1 to 8 there are produced compositions wherein the phenylpropanolamine is replaced by an equivalent active amount of 2-methylamino-1-phenylpropanol, 1-(3'-hydroxyphenyl)-2-methylaminoethanol or 1-phenyl-2-diethylaminopropanol, imidazoline derivatives such as naphazoline, xylometazoline or tetryzoline.

I claim:

1. A pharmaceutical composition useful for the treatment of Rhinitis comprising as active agents
   a. 1-methyl-2-[2-(α-methyl-p-chloro-diphenylmethyloxy)ethyl]pyrrolidine in free base form or in pharmaceutically acceptable acid addition salt form, and b) a compound selected from the group consisting of 2-amino-1-phenylalkan-1-ol of 2 to 4 alkanol carbon atoms, wherein the phenyl is unsubstituted or mono- or disubstituted by hydroxy and the amino is unsubstituted or mono- or disubstituted by alkyl of 1 to 4 carbon atoms and imidazoline substituted in the 2-position by phenylalkyl of 1 to 3 carbon atoms, napthylmethyl, or tetraline, or phenylalkyl of 1 to 3 carbon atoms, napthylmethyl or tetraline, nono, di or tri substituted by alkyl of 1 to 4 carbon atoms wherein the weight ratio of active agent a) to active agent b) is from about 1:10 to about 1:60, and a pharmaceutically acceptable carrier therefor.

2. A composition according to claim 1, wherein active agent b) is 2-amino-1-phenylpropanol, 2-methylamino-1-phenylpropanol, 1-(3'-hydroxyphenyl)-2-methylaminoethanol or 1-phenyl-2-diethylaminopropanol.

3. A composition according to claim 1, wherein active agent b) is naphazoline, xylometazoline or tetryzoline.

4. A composition according to claim 1, wherein active agent b) is in retard form with respect to active agent a).

5. A composition according to claim 1, wherein said ratio is from about 1:25 to about 1:50.

6. A composition according to claim 5, wherein said ratio is from about 1:30 to about 1:50.

7. A composition according to claim 1, in unit dosage form having about 1 mg of active agent b) and from about 30 to about 50 mg of active agent b).

8. A composition according to claim 7, having a core containing active agent b) and a layer outside the core containing active agent a).

9. A coated tablet comprising the composition of claim 1 and having a kernel containing active agent b) and a coating surrounding the kernel and containing active agent a).

10. A method of treating Rhinitis in animals, which comprises orally administering to an animal in need of said treatment a anti-histaminic effective amount of active agent a) and active agent b) of the composition of claim 1.

11. The method of claim 10 which comprises orally administering a weight ratio of active agent a) to active agent b) of from 1:10 to 1:60.

12. The method of claim 11, wherein active agent a) is orally administered in an amount of from 0.02 to 0.15 mg. per kg. animal body weight a day.

13. The method of claim 12, wherein active agent a) is orally administered in an amount of from 2 to 6 mg. daily.

14. A composition according to claim 1 wherein active agent b) is 2-amino-1-phenylalkan-1-ol of 2 to 4 alkanol carbon atoms, wherein the phenyl is unsubstituted or mono- or disubstituted by hydroxy and the amino is unsubstituted or mono- or disubstituted by alkyl of 1 to 4 carbon atoms.

15. A composition according to claim 14 wherein active agent b) is 2-amino-1-phenylpropanol.

* * * * *